(12) United States Patent
Miller

(10) Patent No.: US 8,471,066 B2
(45) Date of Patent: Jun. 25, 2013

(54) SLURRY PROCESS FOR PHOSPHOROMONOCHLORIDITE SYNTHESIS

(75) Inventor: Glenn A. Miller, South Charleston, WV (US)

(73) Assignee: Union Carbide Chemicals & Plastics Technology LLC

(*) Notice: Subject to any disclaimer, the term of this patent is extended or adjusted under 35 U.S.C. 154(b) by 212 days.

(21) Appl. No.: 12/935,095

(22) PCT Filed: Mar. 17, 2009

(86) PCT No.: PCT/US2009/037345
§ 371 (c)(1),
(2), (4) Date: Sep. 28, 2010

(87) PCT Pub. No.: WO2009/120529
PCT Pub. Date: Oct. 1, 2009

(65) Prior Publication Data
US 2011/0021840 A1 Jan. 27, 2011

Related U.S. Application Data

(60) Provisional application No. 61/040,322, filed on Mar. 28, 2008.

(51) Int. Cl.
C07F 9/34 (2006.01)
(52) U.S. Cl.
USPC .................... 568/12; 558/90; 558/96
(58) Field of Classification Search
USPC ........................ 568/12; 558/96, 90
See application file for complete search history.

(56) References Cited

U.S. PATENT DOCUMENTS

| | | | |
|---|---|---|---|
| 4,599,206 A | 7/1986 | Billig et al. | |
| 4,769,498 A | 9/1988 | Billing et al. | |
| 4,929,745 A | 5/1990 | Keblys et al. | |
| 5,235,113 A | 8/1993 | Sato et al. | |
| 5,391,799 A * | 2/1995 | Pastor et al. | 558/96 |
| 5,663,369 A | 9/1997 | Kreutzer et al. | |
| 5,688,986 A | 11/1997 | Tam et al. | |
| 6,031,120 A | 2/2000 | Tam | |
| 6,881,867 B2 | 4/2005 | Ahlers et al. | |
| 7,196,230 B2 | 3/2007 | Peng et al. | |
| 7,217,828 B2 | 5/2007 | Selent et al. | |
| 7,345,185 B2 * | 3/2008 | Ortmann et al. | 556/404 |
| 7,767,861 B2 * | 8/2010 | Ortmann et al. | 568/10 |
| 8,097,749 B2 * | 1/2012 | Miller | 558/96 |
| 2006/0252969 A1 | 11/2006 | Flores et al. | |
| 2007/0112219 A1 * | 5/2007 | Ortmann et al. | 568/10 |
| 2007/0117995 A1 * | 5/2007 | Ortmann et al. | 556/404 |
| 2007/0129678 A1 | 6/2007 | Olsen | |
| 2009/0247790 A1 | 10/2009 | Miller | |
| 2011/0196166 A1 | 8/2011 | Miller | |

FOREIGN PATENT DOCUMENTS

| | | |
|---|---|---|
| WO | 9611182 | 4/1996 |
| WO | 2009120210 | 10/2009 |

OTHER PUBLICATIONS

Lot, O. et al; Journal of Molecular Catalysis A: Chemical 164 (2000), 125-130.*
Greene et al., "Asymmetric Silylphosphite Esters: Synthesis and Reactivity of (rac-o, o-binaphtholato) POSiR3 (R3=Ph3, (t)BuMe2, Et3)", Synthetic Communications, 23(12), 1651-1657 (1993).
Bredikhin et al., "On the use of seven-membered phosphorous heterocycles based on 2,2' -dihydroxy-1, 1'-binaphthalene and 1,4: 3,6-dianhydro-D-mannitol in the 31P NMR analysis of enantiomeric composition of chiral alcohols", Russian Chemical Bulletin, vol. 47, No. 3, Mar. 1998, pp. 411-416.
Buisman et al, "Rhodium catalysed asymmetric hydroformylation with chiral diphosphite ligands", Tetrahedron: Asymmetry, vol. 4, No. 7, Jul. 1993, 1625-1634.
Beller et al., "Dual catalytic systems for consecutive isomerization-hydroformylation reactions", Chem. Eur. J.,1999, 5, No. 4, pp. 1301-1305.
Lot et al., "New electron-deficient aminophosphonite-phosphite ligands for asymmetric hydroformylation of styrene", Journal of Molecular Catalysis A: Chemical 164, (2000), 125-130.
Korostylev et al, Chiral pyrophosphites-synthesis and application as ligands in Rh(I)-catalyzed asymmetric hydrogenation, Tetrahedron: Asymmetry 14 (2003), 1905-1909.
Cramer et al., "Chiral Phosphites and Phosporamidites Based on the Tropane Skeleton and Their Application in Catalysis", Organometallics 2006, 25, 2284-2291.
Barry et al., "Triphenylphosphine-Tetrachloromethane Promoted Chlorination and Cyclodehydration of Simple Diols", J. Org. Chem., 1981, 46, 3361-3364.
Gerrard et al., "Basic Function of Oxygen in Certain Organic Compounds", Chemistry Department, Norhtern Polytechnic, Holloway, London, N.7, England, Aug. 21, 1959, 1105-1123.
Ahmed et al., "Significance of the Solubility of Hydrogen Halides in Liquid Compounds", J. Appl. Chem., 1970, vol. 20, April p. 109-116.
Van Rooy A, et al., "Bulky Diphosphite-Modified Rhodium Catalysts: Hydroformylation and Characterization", Organometallics, vol. 15, No. 2, Jan. 23, 1996, pp. 835-847.
Buisman et al.; "Hydridorhodiurn diphosphite catalysts in the asymmetric hydroformylation of styrene", J. Chem. Soc. Dalton Trans., 1995, pp. 409-417.

* cited by examiner

*Primary Examiner* — Johann R Richter
*Assistant Examiner* — Pancham Bakshi
(74) *Attorney, Agent, or Firm* — Marie F. Zuckerman; Paul D. Hayhurst

(57) ABSTRACT

A process for preparation of a phosphoromonochloridite in high yield, by contacting phosphorus trichloride ($PCl_3$) with an aromatic diol, such as 2,2'-biphenol, in a slurry, which contains a portion of the aromatic diol in solid form and contains a solution phase containing the remaining portion of the aromatic diol and an organic solvent, under reaction conditions sufficient to produce the phosphoromonochloridite. The slurry comprises less than 5 mole percent of a nitrogen base, calculated on total moles of the aromatic diol, and the organic solvent is selected for its low hydrogen chloride solubility.

15 Claims, No Drawings

SLURRY PROCESS FOR PHOSPHOROMONOCHLORIDITE SYNTHESIS

CROSS REFERENCE TO RELATED APPLICATIONS

This application is a 371 of PCT/US2009/120529 filed Mar. 17, 2009, which claims the benefit of U.S. Provisional Application Serial No. 61/040,322, filed Mar. 28, 2008.

CROSS-REFERENCE TO PRIOR APPLICATION

This application claims the benefit of U.S. Provisional Application No. 61/040,322 filed Mar. 28, 2008.

FIELD OF THE INVENTION

This invention relates generally to a process for preparation of phosphoromonochloridites, which are intermediates for synthesis of organopolyphosphites.

BACKGROUND

Phosphites represent a diverse class of organic phosphorus compounds that are useful as ligands for homogeneous catalysis and as components of plasticizers, flame retardants, UV stabilizers and antioxidants. Phosphites can be further classified as organomonophosphites and organopolyphosphites. Organopolyphosphites are particularly useful for certain homogeneous catalysis; for example, U.S. Pat. No. 4,769,498 generally relates to synthesis of organopolyphosphites and use thereof as ligands in hydroformylation processes.

Phosphoromonochloridites are intermediates for synthesizing organopolyphosphites; see, for example, U.S. Pat. Nos. 6,031,120, 5,663,369, and 4,769,498. A phosphoromonochloridite is typically synthesized in a condensation reaction by contacting phosphorus trichloride ($PCl_3$) with one molar equivalent of a di-alcohol or two molar equivalents of a monoalcohol under reaction conditions highly dependent on the reactivity of the starting alcohol and the resulting phosphoromonochloridite. For each molecule of a phosphoromonochloridite produced, the condensation reaction produces two molecules of hydrogen chloride (HCl). In order for the condensation reaction to achieve high, for example, greater than 90 percent, conversion of the alcohol, HCl needs be removed from the reaction solution.

One approach for HCl removal from the condensation reaction is to neutralize HCl using a nitrogen base, in an amount stoichiometric to or in excess to the theoretical amount of HCl to be produced. See, for example, U.S. Pat. Nos. 5,235,113; 6,031,120, and 7,196,230, U.S patent application publication 2007/0112219 A1, and *Journal of Molecular Catalysis* A: Chemical 164 (2000) 125-130. When a nitrogen base is used, however, the resulting nitrogen base-HCl salt must be removed from the reaction mixture by a filtration procedure, which generates chloride and nitrogen-containing wastes that, in turn, increase cost.

Another approach for HCl removal from the $PCl_3$-alcohol condensation reaction involves heating a mixture of the alcohol and a large excess amount of the $PCl_3$ at a temperature sufficiently high to reflux $PCl_3$ (boiling point (bp): 74-78° C.), which drives off the HCl. In this approach, the nitrogen base is not needed or used. For example, U.S. Pat. No. 4,769,498 discloses a procedure for producing 1,1'-biphenyl-2,2'-diyl phosphoromonochloridite by refluxing a mixture of 2,2'-biphenol with 3.7 molar equivalents (2.7 equivalents in excess) of $PCl_3$. The phosphoromonochloridite product is disclosed to be isolated in 72 mole percent yield, based on moles of 2,2'-biphenol employed, by distillation under reduced pressure. Another procedure, as referenced in Korostyler et al., *Tetrahedron: Asymmetry*, 14 (2003) 1905-1909, and Cramer et al., *Organometallics*, Vol. 25, No. 9 (2006) 2284-2291, synthesizes 4-chlorodinaphtho[2,1-d:1',2'-f][1,3,2]dioxaphosphepine by heating a mixture of 1,1'-bi-2-naphthol and 11.5 molar equivalents of $PCl_3$ at 75-80° C. One undesirable feature of the aforementioned approach involves the need to remove and handle a large excess amount of $PCl_3$, which reacts exothermically with moisture and typically involves additional safety considerations. It would be desirable to reduce the excess amount of $PCl_3$ to be used in the process.

When the $PCl_3$-alcohol condensation reaction uses a solid diol, yet another approach for HCl removal involves: a) dissolving the solid diol either in an aprotic polar organic solvent, preferably tetrahydrofuran (THF), or in a solvent mixture comprising an aprotic polar organic solvent, to produce a feed solution; and b) adding the feed solution slowly into a refluxing solution of $PCl_3$ dissolved in a hydrocarbon solvent, such as toluene. The refluxing is required to drive off the HCl as a gas from the reaction solution. The aprotic polar organic solvent, such as THF, is generally required to obtain a feed solution containing greater than about 20 weight percent of the diol at ambient temperature, based on the weight of the feed solution, particularly if the diol has an unacceptable solubility in the hydrocarbon solvent. This process has been used commercially and is the subject of U.S. Provisional Patent Application 61/040,304, filed Mar. 28, 2008, for "ISOTHERMAL PROCESS FOR PHOSPHOROMONOCHLORIDITE SYNTHESIS," filed in the name of Union Carbide Chemicals and Plastics Technology LLC.

With reference to the aforementioned commercial process, hydrogen chloride is known to react with the preferred aprotic polar organic solvent, namely, tetrahydrofuran, to produce 4-chlorobutanol; see, for example, Barry et al., *Journal of Organic Chemistry* (1981), 46(16), 3361-4. Hydrogen chloride reacts with tetrahydrofuran more slowly at lower temperatures, if other conditions remain the same; however, operating at temperatures lower than about 98° C. can lead to accumulation of hydrogen chloride in the reaction solution in the form of THF-HCl complexes, which in turn can lead to an even higher rate of 4-chlorobutanol production. Disadvantageously, both $PCl_3$ and the phosphoro-monochloridite react with 4-chlorobutanol to produce undesirable by-products.

The phosphoromonochloridite is desirably used without further purification in the synthesis of organopolyphosphites. Formation of 4-chlorobutanol, however, during the phosphoromonochloridite condensation reaction not only reduces the yield of phosphoromonochloridite product, preferably, 1,1'-biphenyl-2,2'-diyl phosphoromonochloridite, but also complicates subsequent organopolyphosphite synthesis reactions.

As a further aspect of the aforementioned commercial process, any mixture of $PCl_3$ and THF recovered from the process typically is not reused due to the need to separate $PCl_3$ (bp: 74-78° C.) and THF (bp: 65-67° C.).

In view of the above, a need exists in the art for a more efficient process of producing a phosphoromonochloridite.

SUMMARY OF THE INVENTION

The present invention provides for a novel synthetic process for preparing a phosphoromonochloridite comprising contacting phosphorus trichloride ($PCl_3$) with an aromatic diol represented by formula I:

Formula I

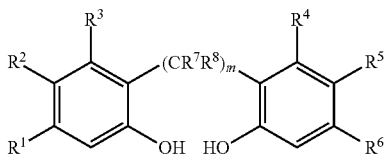

wherein:
m is zero, 1 or 2;
R$^1$, R$^2$, R$^3$, R$^4$, R$^5$, R$^6$, R$^7$ and R$^8$ are each independently selected from hydrogen, halogen, and C$_1$-C$_{10}$ substituted or unsubstituted hydrocarbyl moieties;
and wherein optionally, R$^2$ can be bonded to R$^3$ to form a substituted or unsubstituted hydrocarbylene moiety so as to form a 5- or 6-membered ring; and/or
optionally, R$^4$ can be bonded to R$^5$ to form a substituted or unsubstituted hydrocarbylene moiety so as to form a 5- or 6-membered ring.

in a slurry comprising a portion of the aromatic diol in solid form and comprising a solution phase comprising the remaining portion of the aromatic diol and an organic solvent, wherein the slurry comprises less than 5 mole percent of a nitrogen base, calculated on total moles of the aromatic diol, and the organic solvent has a low hydrogen chloride solubility; the contacting being conducted under reaction conditions sufficient to produce a phosphoromonochloridite represented by formula II:

Formula II

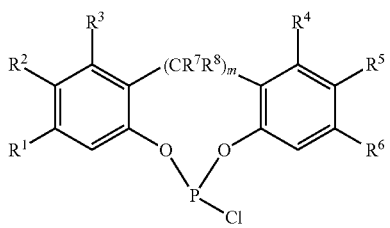

wherein m and R$^1$ through R$^8$ have the definitions given hereinabove.

DETAILED DESCRIPTION OF THE INVENTION

The process of the invention, which hereinafter is referred to simply as "the process," employs an aromatic diol, phosphorus trichloride (PCl$_3$), and an organic solvent.

In describing the present invention, certain phrases, terms, and words are used that are defined herein. When interpreting a meaning of a phrase, term, or word, its definition here governs unless, for a particular use, a different meaning is stated elsewhere in this specification or unless a context of the use of the phrase, term, or word clearly indicates a different meaning is intended from the definitions provided herein.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises "an" aromatic diol can be interpreted to mean that the aromatic diol includes "one or more" aromatic diols. The term "or" refers to members in a list either singly or in any combination.

A "hydrocarbyl" moiety is defined as a monovalent moiety derived from a hydrocarbon by removal of one hydrogen atom from one carbon atom. A "hydrocarbon" shall have its ordinary meaning referring to a compound composed of carbon and hydrogen atoms.

A "hydrocarbylene" moiety is defined as a divalent moiety derived from a hydrocarbon by removal of two hydrogen atoms from two carbon atoms.

A "substituted hydrocarbyl" or "substituted hydrocarbylene" moiety means that one or more H or C atoms in the hydrocarbyl or the hydrocarbylene is substituted by one or more heteroatoms or one or more functional groups that contain one or more heteroatoms, which include, but are not limited to, nitrogen, oxygen, sulfur, phosphorus, boron, chlorine, bromine, and iodine. A substituted hydrocarbyl moiety can be a "hydrocarbyloxy" moiety, which has a generic formula of RO—, wherein R is a hydrocarbyl or substituted hydrocarbyl moiety as defined hereinabove.

A "low hydrogen chloride solubility" in an organic solvent is defined as less than 0.2 moles of hydrogen chloride (HCl) per mole of solvent at a temperature of 20 degrees Celsius (° C.) and a total pressure of 760 millimeters of mercury (mm Hg) (101 kPa). The minimum hydrogen chloride solubility is not critical and may be effectively 0 moles of HCl per mole of solvent at a temperature of 20 degrees Celsius (° C.) and a total pressure of 760 millimeters of mercury (mm Hg) (101 kPa).

The term "organic solvent" has its ordinary meaning referring to an organic substance that is a liquid at ambient temperature and pressure and that is capable of dissolving another substance (solute) to form a uniformly dispersed mixture (solution) at a molecular or ionic level.

The term "ambient temperature" denotes a temperature of 22° C.±2° C.

The term "aprotic" refers herein to an organic solvent that does not donate protons.

Referring to an organic solvent, the term "boiling point" means the temperature at which the vapor pressure of the liquid phase equals a defined pressure of 1 atmosphere.

A "nitrogen base" is defined as a nitrogen-containing organic compound that is capable of neutralizing HCl to form a salt that is essentially insoluble in an organic solvent employed in the process.

The process employs an aromatic diol represented by formula I:

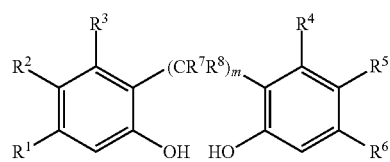

wherein m is zero, 1 or 2;
R$^1$, R$^2$, R$^3$, R$^4$, R$^5$, R$^6$, R$^7$ and R$^8$ are each independently selected from hydrogen, halogen, and C$_1$-C$_{10}$ substituted or unsubstituted hydrocarbyl moieties;
and optionally, R$^2$ can be bonded to R$^3$ to form a substituted or unsubstituted hydrocarbylene moiety so as to form a 5- or 6-membered ring; and/or optionally, $R^4$ can be bonded to $R^5$ to form a substituted or unsubstituted hydrocarbylene moiety so as to form a 5- or 6-membered ring.

Preferably, m is zero or 1, and $R^7$ and $R^8$ are each hydrogen. More preferably, m is zero or 1, and $R^1$, $R^6$, $R^7$ and $R^8$ are each hydrogen.

Examples of aromatic diols that can be employed in the process include, but are not limited to 2,2'-biphenol, 5,5'-dimethyl-2,2'-biphenol, 5,5'-dichloro-2,2'-biphenol, 5,5'-dibromo-2,2'-biphenol, 5,5'-diiodo-2,2'-biphenol, 5,5'-diethyl-2,2'-biphenol, 5,5'-di-n-propyl-2,2'-biphenol, 5,5'-di-isopropyl-2,2'-biphenol, 5,5'-di-n-butyl-2,2'-biphenol, 5,5'-di-sec-butyl-2,2'-biphenol, 5,5'-di-iso-butyl-2,2'-biphenol, 5,5'-di-tert-butyl-2,2'-biphenol, 5,5'-di-n-amyl-2,2'-biphenol, 5,5'-bis(1,1-dimethylpropyl)-2,2'-biphenol, 5,5'-bis(2,2-dimethylpropyl)-2,2'-biphenol, 5,5'-di-n-hexyl-2,2'-biphenol, 5,5'-di-2-hexyl-2,2'-biphenol, 5,5'-di-3-hexyl-2,2'-biphenol, 5,5'-di-n-heptyl-2,2'-biphenol, 5,5'-di-2-heptyl-2,2'-biphenol, 5,5'-di-3-heptyl-2,2'-biphenol, 5,5'-di-4-heptyl-2,2'-biphenol, 5,5'-di-n-octyl-2,2'-biphenol, 5,5'-di-2-octyl-2,2'-biphenol, 5,5'-di-3-octyl-2,2'-biphenol, 5,5'-di-4-octyl-2,2'-biphenol, 5,5'-bis(1,1,3,3-tetramethylbutyl)-2,2'-biphenol, 5,5',6,6'-tetramethyl-2,2'-biphenol, 5,5'-diphenyl-2,2'-biphenol, 5,5'-bis(2,4,6'-trimethylphenyl)-2,2'-biphenol, 5,5'-dimethoxy-2,2'-biphenol, 5,5'-diethoxy-2,2'-biphenol, 5,5'-di-n-propoxy-2,2'-biphenol, 5,5'-di-isopropoxy-2,2'-biphenol, 5,5'-di-n-butoxy-2,2'-biphenol, 5,5'-di-sec-butoxy-2,2'-biphenol, 5,5'-di-iso-butoxy-2,2'-biphenol, 5,5'-di-tert-butoxy-2,2'-biphenol, 1,1'-bi-2-naphthol, bis(2-hydroxyphenyl)methane, 2,2'-methylenebis(4-chlorophenol), and 2,2'-methylenebis(4-tert-butyl-phenol). One preferred species of aromatic diol is 2,2'-biphenol.

Phosphorus trichloride, as may be obtained from any commercial supplier, is also required for the process of this invention. The molar ratio of $PCl_3$ to the total aromatic diol employed in the process advantageously is greater than about 1.0, preferably greater than about 1.1, and more preferably greater than about 1.2; and advantageously is less than 3.5, preferably less than 3.3, more preferably less than 3.1, still more preferably less than about 2.9, still more preferably less than about 2.7, still more preferably less than about 2.5, still more preferably less than about 2.3, still more preferably less than about 2.1, and still more preferably less than about 1.9. As compared with the prior art, the aforementioned molar ratios of $PCl_3$ to total aromatic diol advantageously reduce the amount of excess unconverted $PCl_3$ to be removed upon completion of the condensation reaction.

While on one hand as seen above, a lower excess amount of $PCl_3$ to total aromatic diol is desirably employed; on the other hand, it is desirable to maintain a high molar ratio of $PCl_3$ to the dissolved aromatic diol in the solution phase of the condensation reaction to minimize side reactions of the aromatic diol with the phosphoromonochloridite reaction product. For example, 2,2'-biphenol can react with its reaction product, 1,1'-biphenyl-2,2'-diyl phosphoromonochloridite, to produce undesirable side products: 2'-(dibenzo[d,f][1,3,2]dioxaphosphepin-6-yloxy)biphenyl-2-ol (formula III) and 2,2'-bis(dibenzo[d,f][1,3,2]dioxaphosphepin-6-yloxy)biphenyl (formula IV).

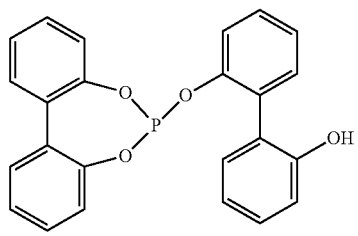

Formula III

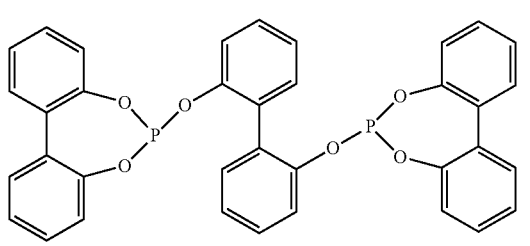

Formula IV

In selecting an organic solvent (and quantity thereof) that maintains a portion of the aromatic diol in a slurry, i.e., partitioned between solid and solution phases, the process advantageously reaps the benefit of having a high molar ratio of $PCl_3$ to the dissolved aromatic diol in the solution or reaction phase, while at the same time reaping the aforementioned benefit of having an overall lower excess amount of $PCl_3$ relative to total aromatic diol.

Accordingly, desirable functions of the organic solvent in the process include, but are not limited to: a) reducing the concentration of the aromatic diol in the solution phase to maintain a high molar ratio of $PCl_3$ to the dissolved aromatic diol in the solution phase during the course of the condensation reaction, and b) facilitating the release of HCl from the condensation reaction solution. To perform at least one of the above described functions, the organic solvent for the process can be selected based on the following criteria: a) the solubility of the aromatic diol in the organic solvent is greater than about 1 percent, preferably greater than about 2 percent, and more preferably greater than about 3 percent, but less than about 50 percent, by weight, based on the weight of the solution at 25° C.; and b) the solubility of HCl in the organic solvent is less than about 0.2, preferably less than about 0.1 mole of HCl per mole organic solvent at a temperature of 20° C. and a total pressure of 760 mm Hg (101 kPa).

The solubility of the aromatic diol in the organic solvent can be measured by using known procedures. For example, the solubility of the aromatic diol in the organic solvent at a specific temperature can be determined by an equilibrium solubility method, which employs a saturated solution of the aromatic diol, obtained by stirring an excess amount of the aromatic diol in the organic solvent at the specific temperature for a sufficient period of time until equilibrium is achieved. Thereafter, the resulting liquid phase saturated solution, the resulting solid phase, or both liquid and solid phases are analyzed by any conventional analytical method to arrive at the solubility of the aromatic diol in the organic solvent.

Procedures for determining HCl solubility in an organic solvent are also well known. For example, bubbler procedures were used by Gerrard et al. (*Chem. Rev.,* 1959, 59, 1105) and Ahmed et al. (*J. Appl. Chem.,* 1970, Vol. 20, April, page 109-116.) for measuring HCl solubility in many organic solvents. Examples of HCl solubility in organic solvents reported by Gerrard et al. and Ahmed et al. are shown in Table 1.

TABLE 1

HCl Solubility in Organic Solvents
at a total pressure of 760 mm Hg (101 kPa)

| Organic solvent | HCl solubility Mol/mol organic solvent | |
| --- | --- | --- |
| | At 10° C. | At 20° C. |
| n-Heptane | 0.02 | 0.015 |
| n-Decane | 0.028 | — |
| Benzene | 0.053 | 0.047 |
| Toluene | 0.07 | 0.051 |
| m-Xylene | 0.08 | 0.071 |
| o-Xylene | 0.08 | 0.061 |
| p-Xylene | 0.08 | 0.064 |
| Chlorobenzene | — | 0.033 |
| Tetrahydrofuran | 1.38 | — |
| Dioxane | 1.05 | — |
| Di-n-butyl ether | 0.89 | — |
| Dibenzyl ether | 0.54 | — |
| Methyl phenyl ether | 0.16 | — |
| Ethyl acetate | 0.66 | — |

Additional desirable functions of the organic solvent used in the process include, but are not limited to, a) keeping the phosphoromonochloridite of formula II in the reaction solution; and b) simplifying isolation of the phosphoromonochloridite as a solution in the organic solvent by simplifying removal of any excess amount of $PCl_3$. Advantageously, the organic solvent selected for the process has a boiling point above about 90° C., preferably above about 95° C., and more preferably above about 100° C., but preferably less than about 250° C., so that any excess $PCl_3$ used in the process can be preferentially removed from the reaction solution to obtain a product solution substantially comprising the phosphoromonochloridite and the organic solvent.

The organic solvent advantageously is selected from hydrocarbon solvents and chlorinated hydrocarbon solvents. Toluene, chlorobenzene, o-xylene, m-xylene, p-xylene, ethylbenzene, heptane, octane, and mixtures thereof are non-limiting examples of organic solvents that can be employed in the process. Dialkyl ethers, such as dibutyl ether, tetrahydrofuran (THF), and dioxane, are not used in the process due to the high solubility of HCl in such solvents (see Table 1); for example, a solubility greater than 0.2 mole HCl, preferably, greater than about 0.5 mole HCl, per mole solvent at a temperature of 20° C. and a total pressure of 760 mm Hg (101 kPa) is not preferred for the organic solvent. As mentioned hereinbefore, under certain conditions, such as high temperatures, THF disadvantageously reacts with HCl to produce 4-chlorobutanol; see, for example, Barry et al., *Journal of Organic Chemistry* (1981), 46(16), 3361-4. As an alcohol, 4-chlorobutanol is reactive towards the desired phosphoromonochloridite product.

The amount of the organic solvent to be employed in the process is determined in conjunction with the solubility of the aromatic diol in the organic solvent. The amount of the organic solvent advantageously is such that greater than about 1 percent, preferably greater than about 3 percent, and more preferably greater than about 5 percent, and advantageously less than about 50 percent, preferably less than about 40 percent, and more preferably less than about 30 percent, by weight, of the total amount of the aromatic diol is dissolved in the organic solvent. The balance of the aromatic diol exists as a solid phase, thereby forming a slurry. The amount of the organic solvent in the slurry advantageously is greater than about 20 percent, preferably greater than about 25 percent, and more preferably greater than about 30 percent, and advantageously is less than about 95 percent, preferably less than about 90 percent, and more preferably less than about 85 percent, of the slurry by weight, based on the total weight of the slurry, which comprises the aromatic diol in both solid and dissolved forms, $PCl_3$, and the organic solvent. Desirably, the amount of the organic solvent is sufficient to substantially solubilize the phosphoromonochloridite product after substantially all of the aromatic diol is converted. Advantageously, greater than about 90 percent, preferably, greater than about 95 percent, and essentially all, by weight, of the phosphoromonochloridite product is solubilized in the organic solvent. Typically, greater than about 95 percent, preferably, greater than about 98 percent, and more preferably, essentially 100 percent by weight of the total aromatic diol is converted in the reaction.

Generally, the phosphoromonochloridite is more soluble than its starting aromatic diol in the organic solvent employed for the process due to removal of hydrogen-bond-forming hydrogen atoms from the hydroxyl groups of the starting aromatic diol. The solubility of the phosphoromonochloridite in the selected organic solvent can be determined by an equilibrium solubility method as described above. Alternatively, the solubility of the phosphoromonochloridite in the selected organic solvent can be determined by producing the phosphoromonochloridite in a dilute solution of the organic solvent, for example, about 1 percent by weight based on the weight of the dilute solution, and then evaporating the organic solvent from the dilute solution until a saturated solution of the phosphoromonochloridite is obtained. The concentration of the phosphoromonochloridite in the saturated solution can be determined by quantitative $^{31}P$ NMR or simple gravimetric analysis.

In one embodiment of the process, $PCl_3$ is initially contacted at ambient temperature with the slurry comprising the aromatic diol in both solid and dissolved forms, the latter dissolved in the organic solvent. The temperature of the slurry is then raised advantageously in less than about 2 hours, preferably less than about 1.5 hours, but typically greater than about 30 minutes, to a reaction temperature sufficient to produce the phosphoromono-chloride. The reaction temperature advantageously is greater than about 25° C., preferably greater than about 30° C., and advantageously is lower than about 80° C., preferably lower than about 75° C. The contacting advantageously is conducted at the reaction temperature for a reaction time sufficiently long that greater than about 95 percent, preferably greater than about 98 percent, and more preferably, essentially all of the aromatic diol is converted in the reaction. The reaction time advantageously is greater than about 3 hours, preferably greater than about 6 hours, and advantageously is less than about 48 hours, preferably less than about 36 hours.

In another embodiment of the process, $PCl_3$ is initially contacted with the slurry at a temperature advantageously below about 20° C., preferably below about 15° C., more preferably below about 10° C., still more preferably below about 5° C., and still more preferably below about 0° C. The minimum operable temperature lies above the freezing point of the selected organic solvent. Typically, the process is conducted at a temperature greater than about −78° C. These lower initial contacting temperatures prevent any unexpected rise in temperature due to the initial heat of mixing and reaction, which in turn may lead to high initial reaction rates.

High initial reaction rates disadvantageously may increase the extent to which side reactions occur between the aromatic diol and its reaction product.

As the reaction progresses, the portion of the aromatic diol in the solid form advantageously is dissolved over time to maintain a substantially constant concentration of the aromatic diol in the solution phase. The solid aromatic diol advantageously is substantially all dissolved when greater than about 30 percent, preferably greater than about 40 percent, and more preferably greater than about 50 percent, of the aromatic diol is converted in the reaction. After substantially all of the solid aromatic diol is dissolved, the progress of the condensation reaction can be conveniently monitored by taking aliquots of the reaction solution for $^{31}$P NMR analysis (disappearance of PCl$_3$ and appearance of the phosphoromonochloridite).

Contacting PCl$_3$ with the aromatic diol in a slurry having a portion of the aromatic diol in solid form reduces the concentration of the aromatic diol in the solution phase, which reduces by-products formation between the aromatic diol and its reaction product of formula II. By-products of formulae III and IV, which are formed when the aromatic diol is 2,2'-biphenol, can be reduced by the slurry method of this invention.

Generally, the process is carried out at ambient pressure, taken as about 1 atmosphere (101 kPa); but higher or lower pressures may be employed, if desired. Preferably, the reaction is conducted under a blanket of inert atmosphere, such as nitrogen, argon, or helium.

The phosphoromonochloridite produced in the process advantageously is isolated as a solution of the organic solvent by removing excess PCl$_3$, either by evaporation under reduced pressures or by distillation under either atmospheric pressure or reduced pressures. Some of the organic solvent may be removed with the PCl$_3$ to ensure complete removal of PCl$_3$ or to obtain a solution having a preferred concentration of the phosphoromono-chloridite. The removed PCl$_3$ and the removed organic solvent, if any, may be reused for a subsequent phosphoromonochloridite synthesis reaction to increase further the efficiency of the process. A neat phosphoromonochloridite product can be obtained by distillation, if desired. The isolated yield of the phosphoromonochloridite advantageously is greater than about 90 mole percent, and preferably, greater than about 95 mole percent, based on the moles of total aromatic diol employed in the process.

The yield of phosphoromonochloridite in the process can vary depending, at least partially, on levels of trace unidentified impurities in the aromatic diol, which impurity levels vary with the source and/or specific batches of the aromatic diol. It is desirable to obtain consistent yields of phosphoromonochloridite in the high end of the yield range. This has been surprisingly achieved by carrying out the condensation reaction in the presence of a trace amount of a base, preferably, a nitrogen base. Therefore, the process advantageously uses a trace amount of a base, preferably, a nitrogen base. The trace amount of nitrogen base advantageously is less than 5 mole percent, more preferably less than 3 mole percent, based on the total moles of the aromatic diol used in the process. If a nitrogen base is used, then preferably, the trace amount of nitrogen base is greater than about 0.01 mole percent, based on the total moles of the aromatic diol used in the process. Non-limiting examples of nitrogen bases are pyridine, trialkylamine, and N,N-dialkylaniline. When the trace amount of base is employed, the yield of phosphoromonochloridite advantageously is greater than about 93 mole percent, and more preferably greater than about 96 mole percent, based on the total moles of aromatic diol employed in the process.

In the prior art, when a nitrogen base is used to neutralize HCl in a phosphoromonochloridite synthesis process, as for example in, U.S. Pat. Nos. 5,235,113; 6,031,120, and 7,196,230, U.S patent application publication 2007/0112219 A1, and *Journal of Molecular Catalysis* A: Chemical 164 (2000) 125-130, the nitrogen base is generally used in an amount greater than one molar equivalent per molar equivalent of HCl produced. When employed in the present invention, the nitrogen base is not intended for neutralizing the HCl produced in the condensation reaction, because the trace amount of base used is less than 2.5 mole percent of the total moles of HCl produced in the process. If the trace amount of base neutralizes acid(s) present or produced in the condensation reaction, the resulting trace amount of salt(s) produce(s) no detrimental effect on the process and may, in fact, be carried with the phosphoromonochloridite in the organic solvent into a subsequent organopolyphosphite synthesis step.

The phosphoromonochloridite of formula II, isolated from the process of this invention, is useful for preparing organopolyphosphites by condensing the phosphoromonochloridite with an organic poly-hydroxy compound in an organopolyphosphite synthesis reaction. Hydrogen chloride is produced as a co-product of this downstream process. The phosphoromonochloridite can be used either as a solution of the organic solvent or in neat form in the organopolyphosphite synthesis. The organopolyphosphite synthesis reaction advantageously is carried out in the presence of a nitrogen base in an amount sufficient to neutralize essentially all of the HCl produced. Isolation of the organopolyphosphite generally involves a procedure for removing the nitrogen base-HCl salt produced from neutralization either by filtration, or by aqueous workup; see, for example, U.S. Pat. Nos. 6,031,120; 5,663,369, and 4,769,498. It has been found that either salt-removing procedure for isolating the organopolyphosphite is effective in removing any trace amounts of salts carried over with the phosphoromonochloridite.

The process of synthesizing the phosphoromonochloridite described hereinabove has one or more of the following advantages, including: a) employing an organic solvent to reduce the concentration of the aromatic diol in the solution phase of a slurry—thereby resulting in higher phosphoromonochloridite yield and less by-products; b) using a lower molar ratio of PCl$_3$ to the total aromatic diol, as compared with the prior art,—thereby reducing excess amount of PCl$_3$; c) conducting the reaction at lower temperature without refluxing either a solvent or PCl$_3$—thereby simplifying operation and reducing energy need; d) producing little or no nitrogen base-HCl salt—thereby reducing waste and cost; and e) enabling recycle of recovered excess amount of PCl$_3$—thereby further improving efficiency and reducing cost.

Specific Embodiments of the Invention

The following example is illustrative of the present invention and is not to be regarded as limiting thereof. Variations in reaction conditions, such as reactants, temperatures and solvents, will be apparent to those skilled in the art, based on the description and example contained herein. All parts, percentages, and proportions referred to herein are given by weight, unless otherwise indicated.

EXAMPLE 1

Preparation of 1,1'-biphenyl-2,2'-diyl phosphoromonochloridite 2,2'-Biphenol (6.2 g, 33 mmol) is charged into a nitrogen purged, dry 250 ml, 3-necked round-bottom flask equipped with a septum port, a magnetic stir bar, and a reflux condenser, which is topped with a nitrogen inlet and a vent line to a scrubber. Degassed anhydrous toluene (50 ml, 43 g) is added and the resulting slurry is cooled with an ice bath to 0° C., followed by addition of PCl$_3$ (7.1 g, 51 mmol) and then pyridine (0.1 ml, 1 mmol). The resulting slurry, which contains solid 2,2'-biphenol, dissolved 2,2'-biphenol, PCl$_3$ and toluene, is stirred while being warmed to 35° C. over a period of 60 minutes and then stirred at 35° C. overnight, during which time the solid dissolves to give a clear solution. $^{31}$P NMR analysis shows only surplus PCl$_3$ and 1,1'-biphenyl-2,2'-diyl phosphoromonochloridite (δ=180.5 ppm) with less than 5 mole percent impurities. The solution is distilled up to 94° C. to remove excess PCl$_3$ (bp=76°).

What is claimed is:

1. A process for preparing a phosphoromonochloridite comprising contacting phosphorus trichloride (PCl$_3$) with an aromatic diol represented by the formula:

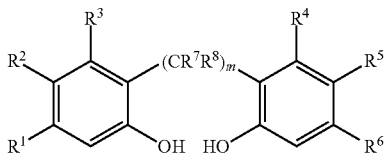

wherein:
m is zero, 1 or 2;
R$^1$, R$^2$, R$^3$, R$^4$, R$^5$, R$^6$, R$^7$ and R$^8$ are each independently selected from hydrogen, halogen, and C$_1$-C$_{10}$ substituted or unsubstituted hydrocarbyl moieties;
and wherein optionally, R$^2$ can be bonded to R$^3$ to form a substituted or unsubstituted hydrocarbylene moiety so as to form a 5- or 6-membered ring; and/or
optionally, R$^4$ can be bonded to R$^5$ to form a substituted or unsubstituted hydrocarbylene moiety so as to form a 5- or 6-membered ring,
in a slurry comprising a portion of the aromatic diol in solid form and comprising a solution phase comprising the remaining portion of the aromatic diol and an organic solvent, wherein the slurry comprises less than 5 mole percent of a nitrogen base, calculated on total moles of the aromatic diol, wherein the organic solvent has a low hydrogen chloride solubility, wherein the molar ratio of the PCl$_3$ to the aromatic diol is greater than about 1.0/1 to less than 3.5/1; and wherein the organic solvent is used in an amount of from greater than about 20 percent to less than about 95 percent of the slurry by weight, based on the weight of the slurry; the contacting being conducted under reaction conditions sufficient to produce a phosphoromonochloridite represented by the formula:

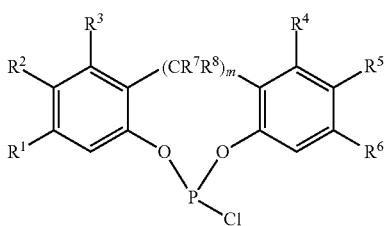

wherein m and R$^1$ through R$^8$ have the definitions given hereinabove,
with the proviso that the reaction time is from greater than about 3 hours to less than about 48 hours, that greater than about 95 mole percent of the aromatic diol is converted in the reaction, and that the contacting is conducted at a reaction temperature from greater than about 25° to less than 75° C.

2. The process of claim 1, wherein m is zero or 1.

3. The process of claim 1, wherein R$^1$, R$^6$, R$^7$ and R$^8$ are each hydrogen.

4. The process of claim 1, wherein the aromatic diol is 2,2'-biphenol.

5. The process of claim 1, wherein the organic solvent has a boiling point of greater than about 90° C. and less than about 250° C.

6. The process of claim 1, wherein the organic solvent is selected from the group consisting of toluene, chlorobenzene, o-xylene, m-xylene, p-xylene, ethylbenzene, heptane, octane, and mixtures thereof.

7. The process of claim 1, wherein the process further comprises contacting PCl$_3$ with the aromatic diol at an initial temperature in a range from greater than about −78° C. to below about 20° C., which is then raised to the reaction temperature from greater than about 25° to less than 75° C.

8. The process of claim 1 wherein the contacting is conducted in the presence of a nitrogen base in an amount from greater than about 0.01 mole percent to less than about 5 mole percent, calculated on total moles of the aromatic diol.

9. The process of claim 8, wherein the nitrogen base is selected from the group consisting of pyridine, trialkylamine, and N,N-dialkylanine.

10. The process of claim 1, wherein the process further comprises removing unreacted PCl$_3$ to obtain a product solution comprising the phosphoromonochloridite and the organic solvent.

11. The process of claim 1, wherein all or a portion of the unreacted PCl$_3$ is recovered and recycled to the process.

12. A process for preparing 1,1'-biphenyl-2,2'-diyl phosphoro-monochloridite, the process comprising contacting PCl$_3$ with 2,2'-biphenol in a slurry, which slurry comprises a portion of the 2,2'-biphenol in solid form and comprises a solution phase comprising the remaining portion of the 2,2'-biphenol and an organic solvent, at a reaction temperature greater than about 25° to less than about 75° C. for a time sufficient to convert greater than about 95 mole percent of the 2,2'-biphenol to 1,1'-biphenyl-2,2'-diyl phosphoromonochloridite; wherein the slurry comprises less than about 5 mole percent of a nitrogen base, calculated on total moles of 2,2'-biphenol, the molar ratio of the PCl$_3$ to 2,2'-biphenol is greater than about 1.0/1 to less than 3.5/1, and wherein the organic solvent is used in an amount of from greater than about 20 percent to less than about 95 percent of the slurry by weight, based on the weight of the slurry, and the organic solvent has a hydrogen chloride solubility of less than about 0.2 mole HCl per mole organic solvent measured at a temperature of 20° C. and a total pressure of 760 mm Hg (101 kPa).

13. The process of claim 12 wherein the slurry comprises at least about 0.01 mole percent of a nitrogen base, calculated on total moles of 2,2'-biphenol.

14. The process of claim 1 wherein the yield to the phosphoromonochloridite is greater than about 90 mole percent.

15. The process of claim 1 wherein the yield to the phosphoromonochloridite is greater than about 95 mole percent.

* * * * *